United States Patent [19]

Stasuk et al.

[11] Patent Number: 5,046,364
[45] Date of Patent: Sep. 10, 1991

[54] HAND-HELD ULTRASONIC PROBE

[76] Inventors: David G. Stasuk, 8275 Burnlake Drive, Burnaby, British Columbia, Canada, V5A 3L1; Roger A. Strukoff, 214-5140 Saunders Street, Burnaby, British Columbia, Canada, V5H 1T2

[21] Appl. No.: 601,455

[22] Filed: Oct. 22, 1990

[51] Int. Cl.⁵ .................. G01N 29/24; G01N 29/04
[52] U.S. Cl. .................................... 73/623; 73/627; 73/629; 73/640; 73/644
[58] Field of Search ............... 73/623, 627, 629, 640, 73/644

[56] References Cited

U.S. PATENT DOCUMENTS

| | | | |
|---|---|---|---|
| 3,584,504 | 6/1971 | Proctor et al. | 73/640 |
| 4,353,257 | 10/1982 | Vrba et al. | 73/623 |
| 4,412,315 | 10/1983 | Flournoy | 73/623 |
| 4,523,470 | 6/1985 | Müller et al. | 73/623 |
| 4,663,727 | 5/1987 | Saporito et al. | 73/623 |
| 4,876,672 | 10/1989 | Petermann et al. | 73/623 |

Primary Examiner—Hezron E. Williams
Assistant Examiner—Rose M. Finley
Attorney, Agent, or Firm—Barrigar & Oyen

[57] ABSTRACT

A hand-held ultrasonic probe for measuring the thickness of a conduit, such as a boiler tube, from the tube inside surface. The probe is slidable and rotatable relative to the longitudinal axis of the tube under investigation. The probe may also be manually skewed relative to the tube longitudinal axis to measure corroded regions which are not parallel to the centerline of the tube.

17 Claims, 8 Drawing Sheets

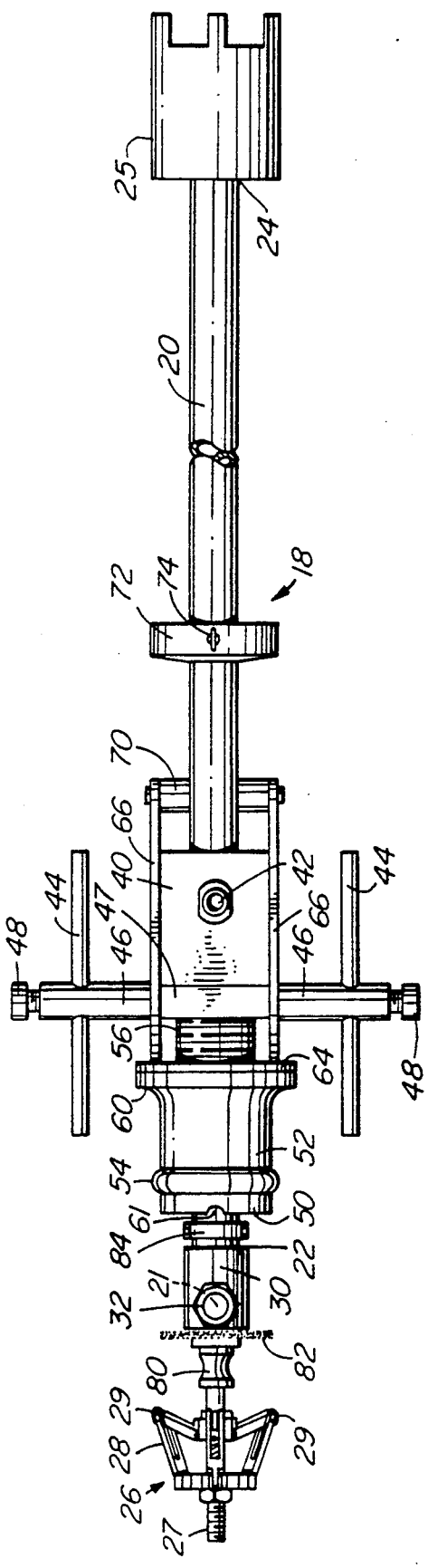
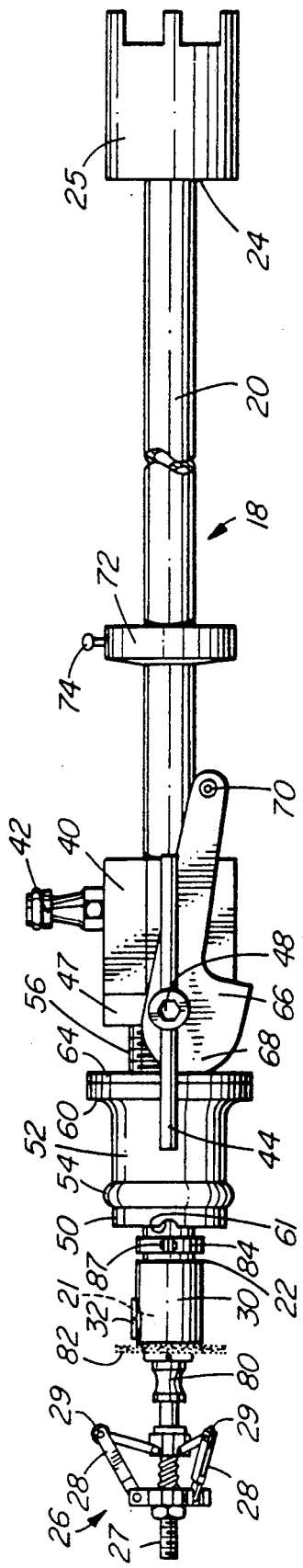
FIG. 5
FIG. 6

HAND-HELD ULTRASONIC PROBE

FIELD OF THE INVENTION

This application pertains to a hand-held ultrasonic probe for non-destructive measurement of the wall thickness of a conduit, such as a boiler tube. More particularly, this application relates to a probe which may be manually skewed relative to the longitudinal axis of the tube under investigation to direct ultrasonic pulses at an oblique angle to the tube inner wall and thereby measure corroded regions not parallel to the centerline of the tube.

BACKGROUND OF THE INVENTION

Large recovery boilers used in pulp and paper mills typically include a densely packed array of generating bank or boiler tubes. Each tube has an open end in communication with a steam or water drum. It has previously been recognized that some boiler tubes are most susceptible to corrosion at their point of attachment to the drum. Accordingly, various ultrasonic probes have been proposed in the past for determining the wall thickness of the boiler tubes in that region.

U.S. Pat. No. 4,353,257 granted to Vrba et al on Oct. 12, 1982 discloses a system for periodically inspecting the thickness of boiler tubes using an ultrasonic probe. The Vrba probe assembly contains a transducer which is mechanically coupled to a motor drive. Rotation of the motor drive causes the transducer to move in a helical path into and out of the boiler tube to be tested. The Vrba probe assembly further includes a carriage which is urged against the tube inner wall by a spring. The purpose of the carriage is to maintain the transducer in the optimum orientation relative to the tube inner wall.

The primary drawback of the Vrba device is that it would not be suitable for accurately measuring corroded tube areas which are not parallel to the centerline of the tube. As a result of the construction of the transducer carriage, the Vrba probe is not optimized for use in tubes having a rolled or undulating contour. The scanning path is entirely controlled by the motor drive and the probe itself is not manually manipulatable.

U.S. Pat. No. 4,663,727 granted to Saporito et al on May 5, 1987 is also exemplary of the prior art. This reference discloses an ultrasonic inspection system employing a transducer mounted at one end of an elongate probe connected to a rotational and axial drive mechanism. No means are provided for manually skewing the probe out of alignment with the longitudinal axis of the tube to be inspected to detect corroded areas not parallel to the centerline of the tube.

U.S. Pat. No. 4,412,315 granted to Flournoy on Oct. 25, 1983 discloses an acoustic pulse-echo wall thickness method and apparatus for detecting anomalies, such as pits, in pipelines. The apparatus includes a transducer capable of generating simultaneous acoustic pulses in opposite directions and two reflectors for reflecting the acoustic pulses toward the inner wall of the pipe under inspection. One of the pulses is directed in a path normal to the pipe wall and the other is reflected in a path oblique to the pipe wall. The Flournoy device is thus capable of measuring wall thickness and simultaneously determining the presence of anomalies in the wall being surveyed. However, it suffers from the disadvantage that ultrasonic pulses may be directed at the pipe inner wall only at a single oblique angle, as determined by the orientation of the reflector face. If it was desired to direct scanning pulses at a plurality of oblique angles, then a plurality of transducers and reflector surfaces would be required.

Accordingly, the need has arisen for a hand-held ultrasonic probe incorporating a single transducer which may be manually skewed relative to the longitudinal axis of the tube to direct ultrasonic acoustic pulses at a plurality of oblique angles relative to the tube inner wall and thereby accurately identify corroded tube areas which are not parallel to the longitudinal axis of the tube.

SUMMARY OF THE INVENTION

In accordance with the invention, there is provided a hand-held probe for inspecting the thickness of an elongate conduit having an open outer end in communication with the interior of a drum. The probe has an apertured housing and an elongate hollow wand adapted for sliding reciprocal movement through the housing along the longitudinal axis of a conduit and for rotational movement relative to the housing and the conduit. A transducer for transmitting and receiving ultrasonic signals is mounted at an inner end of the wand transversely to the wand longitudinal axis. The transducer is connectable to an ultrasonic signal processing instrument remote from the probe.

The probe also includes sealing means encircling the wand at an axial position thereof for releasably sealing the conduit outer end, liquid delivery means connectable to an inlet on the housing for providing coupling liquid to and drawing liquid from a portion of the conduit above the sealing means which includes the transducer, and self-centering means coupled to the inner end of the wand for centering the wand coaxially with the conduit such that ultrasonic pulses generated by the transducer are ordinarily transmitted in a path normal to the inner surface of the conduit.

The wand is manually pivotable about the sealing means away from a scanning position coaxial with the conduit to a scanning position offset from the longitudinal axis of the conduit such that the ultrasonic pulses generated by the transducer are transmitted in a path oblique to the conduit inner surface.

Preferably the sealing means encircles the wand at an axial position between the transducer and the housing. The sealing means may include an inner collar threadedly connectable to the inner end of the housing having a radial groove at a position remote from the housing, a resiliently deformable annular gland positionable in the inner collar groove for radially engaging the conduit inner surface, and an outer collar surrounding a central portion of the inner collar, the outer collar having an inner end bearing against the annular gland. Advantageously, the outer diameter of the outer collar is less than the inner diameter of the conduit. Alternatively, the outer collar may have an enlarged flange at its outer end having an outer diameter greater than the conduit inner diameter.

Preferably, the probe further includes compression means connected to the housing for axially compressing the outer collar to cause radial compression of the annular gland against the conduit inner surface. The compression means may include a pair of arms pivotally coupled to the housing on opposite lateral sides thereof, each of the arms having an inner camming surface bearing against the outer collar. The compression means may also include a handle extending between the arms for actuating simultaneous pivotal movement of the arms.

Advantageously, the inner collar is rotatable relative to the housing to adjust the longitudinal displacement between the compression means and the annular gland.

Preferably, the outer end of the housing sealingly engages the wand.

The self-centering means may include a tripod encircling the wand having spaced-apart radially extensible and retractable arms for frictionally engaging the conduit inner surface. Preferably the tripod arms are biased to the extended position.

The probe may also include an enlarged handle located at the wand outer end to enable manual manipulation of the wand. An inward travel ring encircling the wand and slidably adjustable along the longitudinal axis between the housing and handle may also be provided. The limit ring is lockable at a selected axial position on the wand, and includes a marking at one circumferential position which may be aligned with the transducer for indicating the orientation of the transducer when the wand is rotated within the conduit.

The probe may also include an outward travel limit ring encircling the wand and slidable along the longitudinal axis of the wand between the transducer and the sealing means. The outward travel limit ring is also lockable at a selected axial position on the wand.

The probe may also include a pair of elongate rods mounted on opposed sides of the housing in a plane generally parallel to the longitudinal axis of the housing. The rods are longitudinally adjustable relative to the housing such that the inner ends of the rods contact the inner surface of the drum on either side of the conduit when the probe is placed in operative scanning position within the tube.

BRIEF DESCRIPTION OF THE DRAWINGS

In drawings which illustrate a specific embodiment of the invention, but which should not be construed as restricting the spirit or scope of the invention in any way.

FIG. 5 is a bottom, plan view of the probe of FIG. 4;

FIG. 6 is a side elevational view of the probe of FIG. 4;

DETAILED DESCRIPTION OF THE PREFERRED EMBODIMENT

Figure 1:
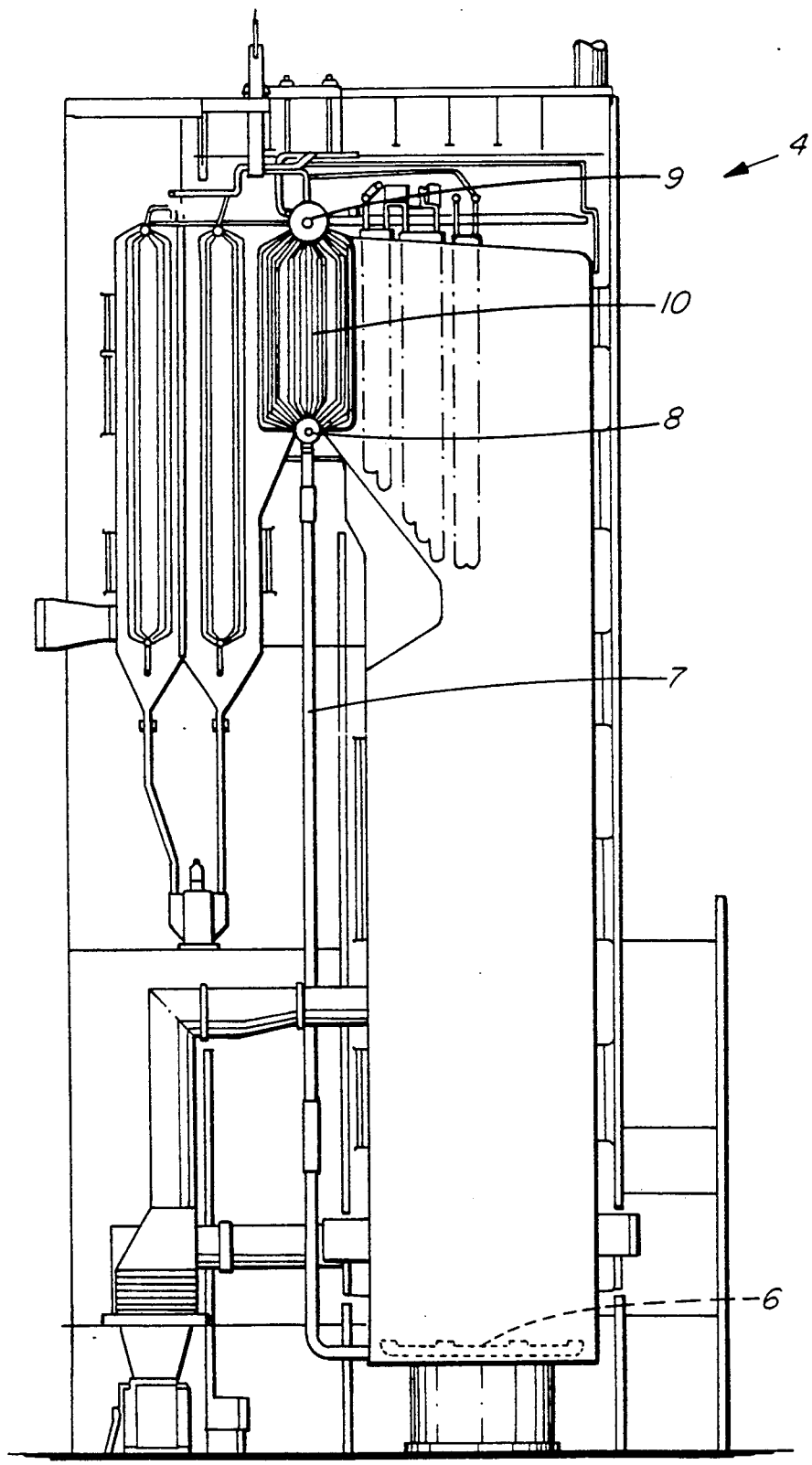
FIG. 1 is a schematic side view of a typical recovery boiler used in the pulp and paper industry having a plurality of boiler tubes in communication with a lower water drum.
Figure 2:
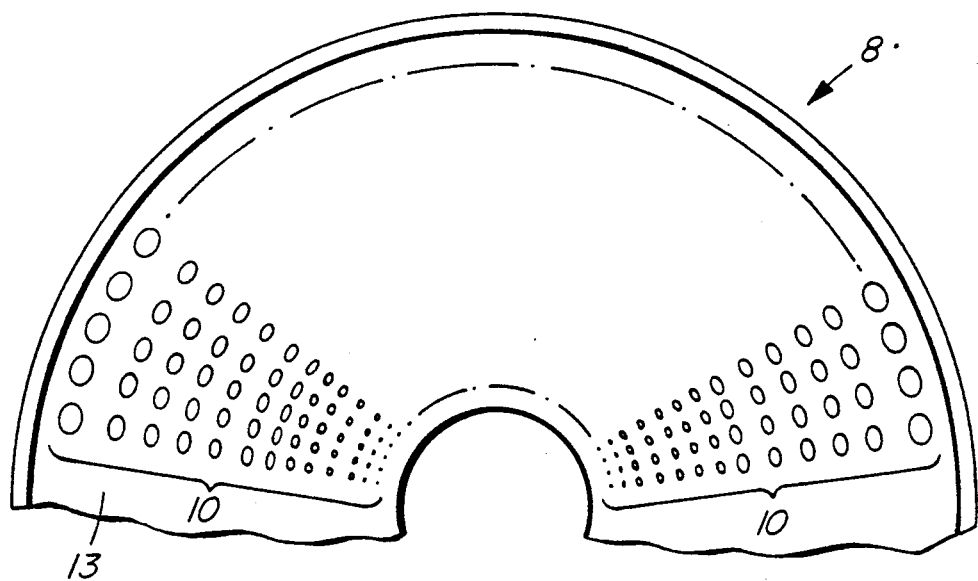
FIG. 2 is a fragmented, perspective of the drum of FIG. 1 illustrating a plurality of vertically inclined boiler tubes each having an open end on the upper circumferential surface of the drum.

FIG. 1 illustrates a chemical recovery boiler 4 typically used in the pulp and paper industry to recover chemical reagents used during the paper making process and to burn organic waste. Chemicals burning in a lower recovery furnace chamber 6 generate a high degree of heat which rises through the furnace 7 to heat a lower cylindrical water drum 8. Drum 8 contains a volume of water under pressure. A densely packed array of generating tubes 10 are connected to the upper circumferential surface of lower drum 8 (FIG. 2). Water within the lower portion of generating bank tubes 10 is converted to steam which is conveyed by the same tubes 10 to an upper drum 9 (FIG. 1). The steam may be used to drive the turbine of an electrical generator or may be diverted to drive other machinery used in the paper making process.

Figure 3:
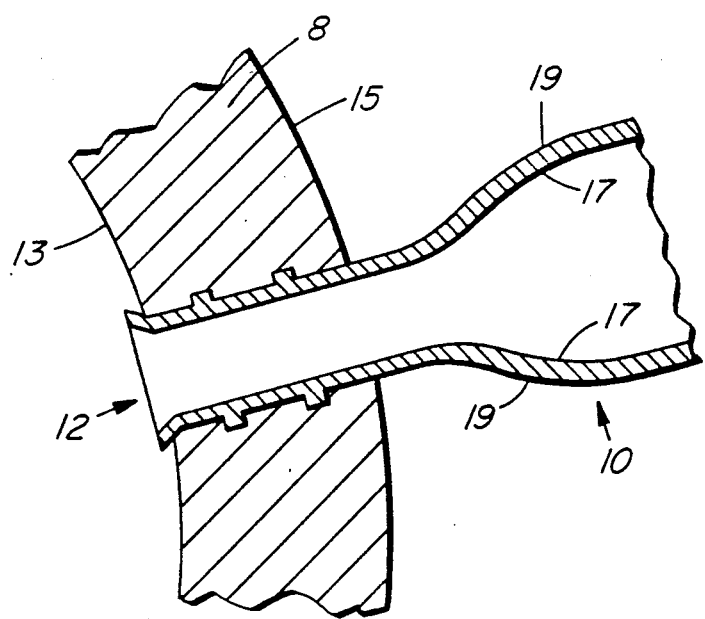
FIG. 3 is an enlarged, fragmented view of a single boiler tube at its point of attachment to the drum of FIGS. 1 and 2.

As shown in FIG. 3, each generating bank tube 10 has an open end 12 which is in communication with the interior of lower drum 8. Lower drum 8 is typically a cylindrical sheet of metal between 2 and 5 inches in thickness having an inner surface 13 and an outer surface 15. Typically each tube 10 projects for a short distance from drum inner surface 13 within the interior of drum 8.

Generating tubes 10 have a tendency to corrode near their point of attachment to drum outer surface 15. If a tube 10 bursts, pressurized water is vented to atmosphere which may cause explosive reactions when the water rains down on the furnace molten chemical bed located below lower drum 8. It is necessary to disable boiler 4 entirely in order to replace a burst generating tube 10 which results in substantial downtime and consequent loss of revenues.

Accordingly, it is imperative that the generating tubes 10 be routinely inspected at their point of attachment to lower drum 8 to identify tubes 10 with corroded walls. Tubes 10 with wall portions below a minimum acceptable thickness are then replaced during routine maintenance before bursting occurs.

Figure 4:
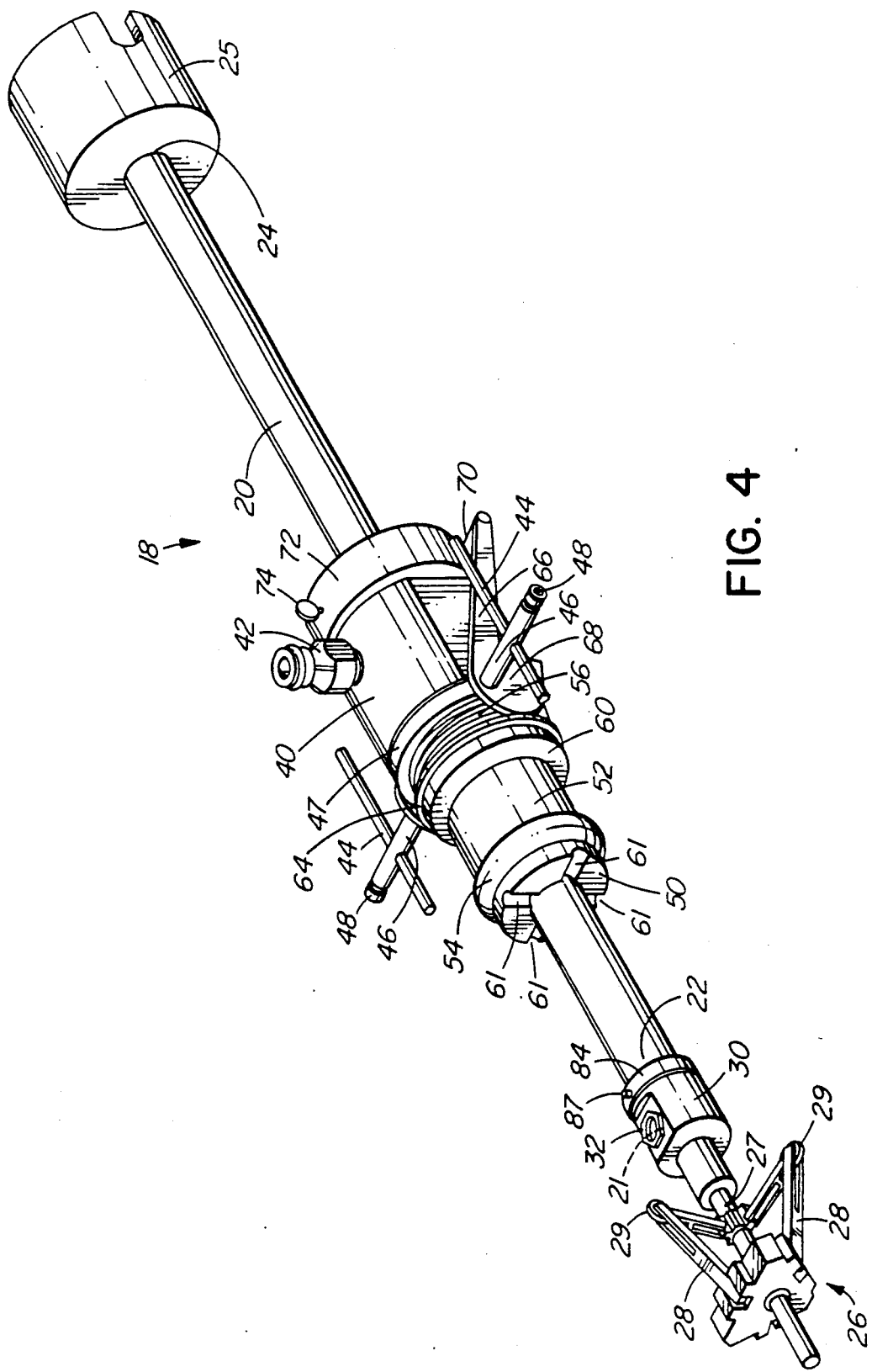
FIG. 4 is a bottom, isometric view of an ultrasonic probe constructed in accordance with the invention.

Lower drums 8 typically used in pulp and paper mill boilers are usually of sufficient size to allow maintenance inspectors to enter the lower drum 8 and manually insert a probe into the open outer end 12 of tubes 10 after the drum 8 has been drained of water. With reference to FIGS. 4 and 5, the present invention is directed to a hand-held probe generally designated 18 for successively measuring the thickness of tubes 10 from within lower drum 8. Probe 18 employs a single, built-in pulse-echo transducer 21 for transmitting and receiving ultrasonic waves. The thickness of tube 10 to be inspected can be determined by monitoring the intervals between successive sound pulses and the amplitude of sound pulses reflected off the inner wall 17 and outer wall 19 of tube 10.

In order for transducer 21 to operate properly, it must be coupled to the inner wall 17 of tube 10 by a liquid medium in order to facilitate transmission of the ultrasonic waves. As described in further detail below, probe 18 includes means for sealing the outer, open end 12 of tube 10 to be inspected and for introducing liquid into tube 10 to provide a coupling medium.

As indicated above, tubes 10 are usually arranged in an array on the upper circumferential surface of lower drum 8 so that they are upwardly inclined relative to the longitudinal centerline of lower drum 8. Thus, if the outer end 12 of tube 10 to be inspected is sealed and a volume of water is introduced into tube 10, it will be maintained by gravitational forces at the tube outer end 12 proximate to drum outer surface 15. Accordingly, it is not necessary to seal an inner portion of tube 10 in order to flood the area to be inspected with coupling medium.

Tubes 10 typically have a rolled surface at their outer end 12 to facilitate insertion into mating apertures machined in lower drum 8 when the boiler is initially fabricated. After tubes 10 are inserted and rolled within lower drum 8, the rolled surface typically extends inwardly (i.e. toward upper drum 9) for a short distance beyond the drum outer wall 15. As a result of the undulating profile of tube 10 in this region, it is often difficult to accurately measure its wall thickness using conventional ultrasonic probes which direct scanning pulses directly perpendicular to tube inner wall 17. As discussed further below, probe 18 of the present invention may be manually skewed away from a scanning position coaxial with tube 10 to enable direction of ultrasonic pulses at an angle oblique to tube inner wall 17. This results in more accurate thickness readings.

With reference to FIGS. 4–6, the structure and operation of ultrasonic probe 18 will now be considered in further detail. Probe 18 consists of an elongate tubular wand 20 having an inner end 22 and an outer end 24. An enlarged knob 25 is provided at the wand outer end 24 so that the wand 20 may be manually manipulated by the maintenance inspector after the wand inner end 22 is inserted into the tube 10 to be inspected.

The wand inner end 22 is integrally connected to a transducer receptacle 30. Preferably wand inner end 22 is permanently secured to transducer receptacle 30 with a suitable adhesive during the initial fabrication of probe 18. Transducer receptacle 30 has a threaded bore hole 31 for receiving a threaded retainer 32 housing transducer 21. Transducer retainer 32 is positioned so that transducer 21 is oriented directly perpendicular to the longitudinal axis of wand 20.

Figure 9:
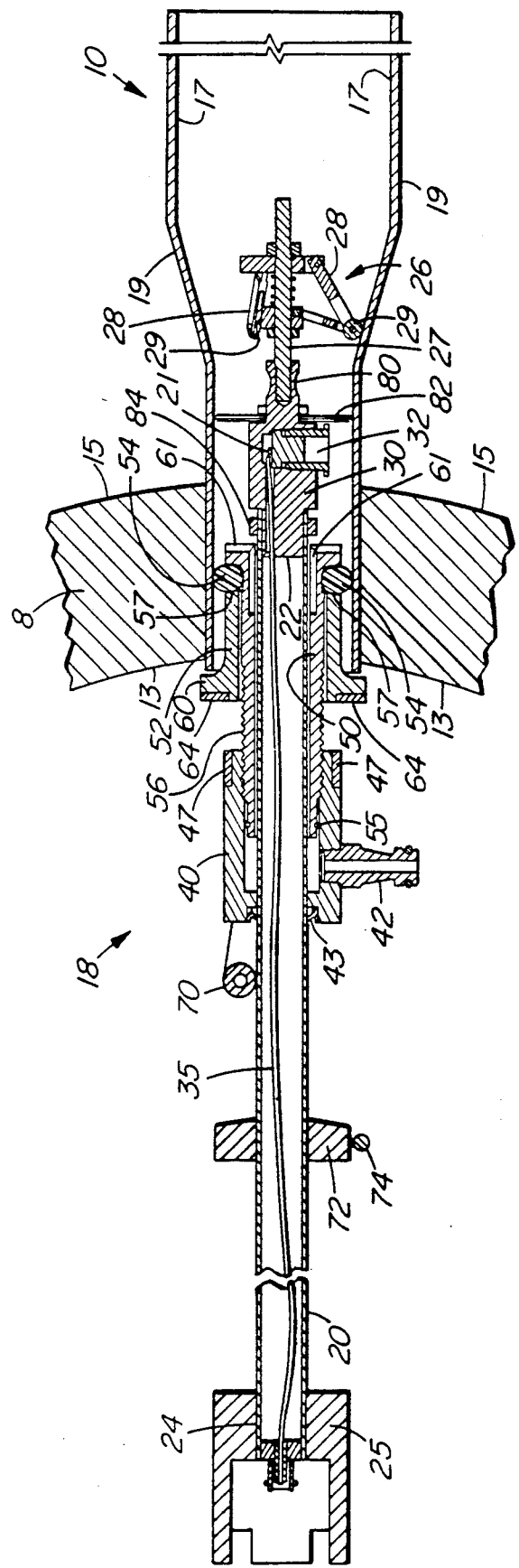
FIG. 9 is a longitudinal section of the probe of FIG. 7.

Transducer 21 is electrically connected to an ultrasonic signal processing instrument (not shown) remote from probe 18 by a length of coaxial cable 35 threaded through the interior of wand 20 (FIG. 9). As shown best in FIG. 10, transducer receptacle 30 has a longitudinal internal bore 33 which enables connection of coaxial cable 35 directly to transducer 21.

Figure 10:
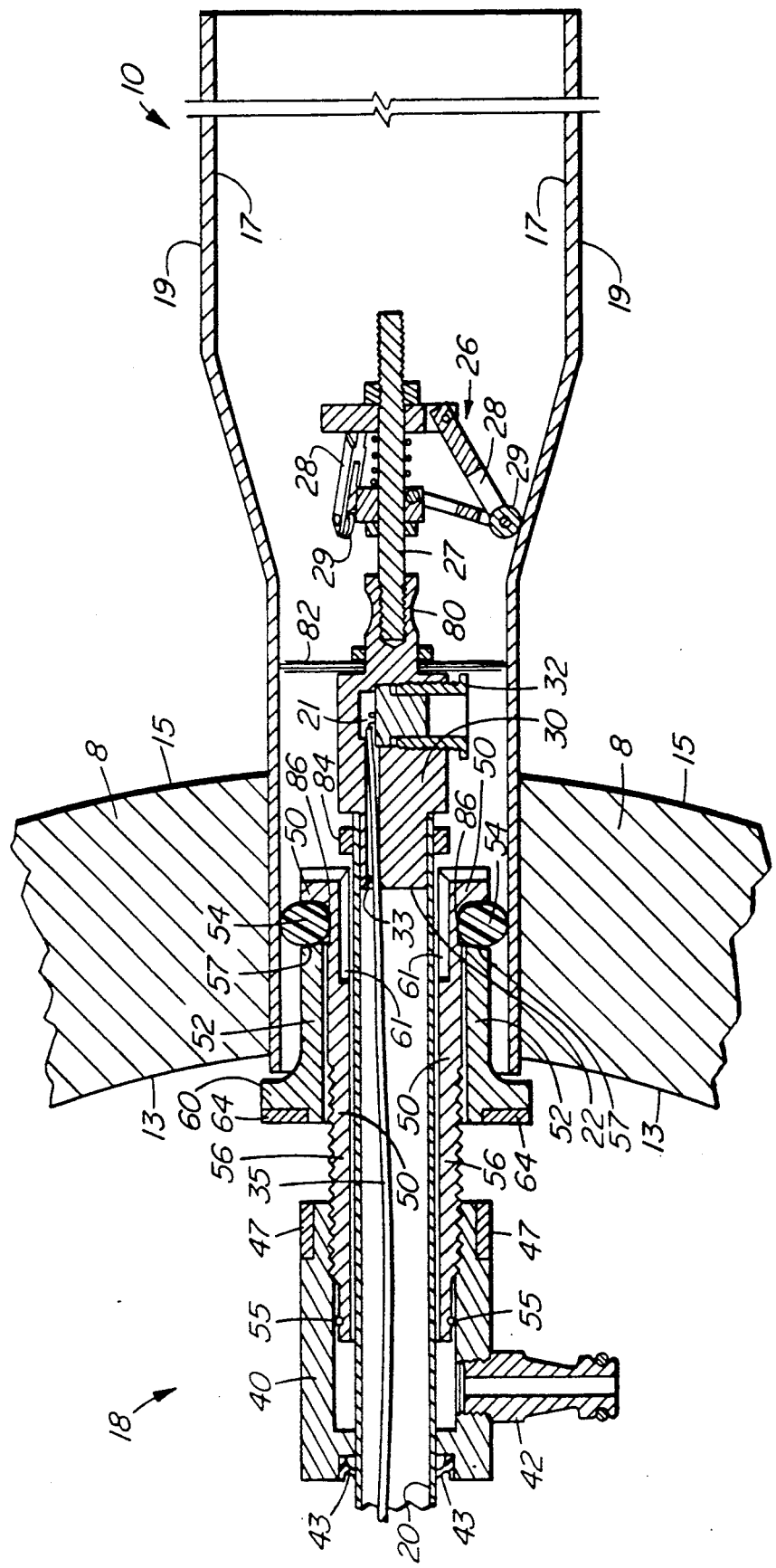
FIG. 10 is an enlarged, longitudinal section of the probe of FIG. 7 showing the inner end of the probe in operative scanning position.

A centering device generally designated 26 is integrally connected to the inner end of transducer receptacle 30. In particular, centering device 26 includes a threaded shaft 27 which is received in a mating bore hole located at the inner end of transducer receptacle 30. Centering device 26 has three equally spaced-apart radially extensible legs 28 which are rotatably mounted on shaft 27. Thus shaft 27 is freely rotatable relative to legs 28 when wand 20 is rotated. Extensible legs 28 are provided for centering wand 20 coaxial with tube 10. Each extensible leg 28, which is ordinarily biased to its extended position, has a roller 29 for frictionally engaging the tube inner wall 17. When probe 18 is withdrawn from tube 10 and legs 28 are retracted to their collapsed position, rollers 29 are seated in a groove 80 located at the inner end of transducer receptacle 30 (FIG. 10). When inserted into a tube 10 having a smaller than usual inside diameter, this feature allows for continued free-wheeling centering action.

Probe 18 further includes an apertured housing 40 for slidably receiving wand 20. Wand 20 is also rotatable about its longitudinal axis within housing 40. As should be apparent from the above description, transducer receptacle 30 and centering device shaft 27 are integrally connected to wand 20 and are slidable and rotatable therewith.

Housing 40 has a threaded vertical bore for receiving a liquid inlet 42 connectable to a liquid supply. Liquid inlet 42 is preferably a quick-disconnect fixture for attaching a standard garden-type hose to probe 18.

An rod wiper type seal 43 is positioned at the outer end of housing 40 for sealingly engaging the outer circumferential surface of wand 20.

As best seen in FIG. 5, probe 18 further includes a pair of elongate drum thickness compensation rods 44 which are positioned on either side of housing 40 in a plane generally parallel to the longitudinal axis of wand 20. Rods 44 are mounted on a shaft 46 extending transversely of housing 40. Shaft 46 is coupled to a fixed mounting ring 47 encircling the inner end of housing 40. Rods 44 are longitudinally adjustable by loosening caps screws 48 and sliding rods 44 relative to housing 40 as desired. Cap screws 48 are then tightened to lock rods 44 in the selected position.

As discussed further below, rods 44 are provided for limiting the degree of reverse travel of wand 20 so that transducer 21 begins scanning tube 10 commencing at the drum outer surface 15 and moving inwardly. Ordinarily, rods 44 are adjusted so that the longitudinal displacement between the rod inner ends and the center of transducer 21 approximates the thickness of drum 8 (i.e. the displacement between drum inner surface 13 and drum outer surface 15).

Probe 18 also includes "sealing means" for sealing the open outer end 12 of tube 10; namely, an inner sealing collar 50, an outer sealing collar 52, and an annular gland 54. Inner sealing collar 50 includes a threaded screw 56 which is received at the outer end of apertured housing 40 as shown best in FIGS. 8–10. The outermost end of inner sealing collar 50 is fitted with an O-ring seal 55 for sealingly engaging the inner wall of housing 40. The outermost end of inner sealing collar 50 has a tapered, circumferential groove 86 which serves as a seat for annular gland 54. As shown best in FIGS. 4 and 7, the innermost end of inner sealing collar 50 is also provided with a series of radial and axially extending slots 61. Since the inner diameter of inner sealing collar 50 at its innermost end is approximately equal to the outer diameter of wand 20, slots 61 are provided to facilitate free flow of coupling liquid from housing liquid inlet 42 to the interior of tube 10.

Outer sealing collar 52 surrounds a central portion of inner sealing collar 50, as shown in FIG. 10, and is slidably displaceable relative to collar 50. The inner end 57 of outer sealing collar 52 bears directly against annular gland 54. The outer end of outer sealing collar 52 is radially flared to define a flange 60 having a diameter exceeding the diameter of the tube 10 to be inspected. Flange 60 is positioned proximate to the outer end 12 of tube 10 when probe 18 is inserted within tube 10 in the operative scanning position. As discussed further below, the outer end of outer sealing collar 52 also has a lip for receiving an annular cam bearing ring 64 (FIG. 10).

As shown best in FIGS. 4–6, probe 18 further includes "compression means"; namely, a pair of arms 66 pivotally coupled on either side of housing 40. In particular, arms 66 are coupled to fixed mounting ring 47 encircling housing 40 at the inner end thereof. Arms 66 include an inner camming surface 68 bearing against ring 64. The outer ends of arms 66 remote from housing 40 are connected by a handle 70 for actuating simultaneous pivotal movement of arms 66 about the transverse axis of housing 40.

Arms 66 are provided for selectively applying axial pressure to camming ring 64 and hence outer sealing collar 52. Sealing collars 50, 52 are preferably constructed from a relatively rigid material, such as acetal plastic. Annular sealing gland 54, by contrast, is preferably constructed from a resiliently deformable material. Accordingly, when outer sealing collar 52 is axially compressed, its inner end 57 is forced against sealing gland 54 which causes radial expansion of sealing gland 54. Sealing gland 54 is thus sealingly engaged against tube inner wall 17. This compensates for small variations in the inside diameter of tubes 10 to ensure adequate sealing and locking of probe 18 within tube 10.

In the operative position, radial compression of annular gland 54 against tube inner end 17 is sufficient to counteract gravitational forces acting against probe 18 when it is inserted within a vertically inclined tube 10. The degree of compression of annular sealing gland 54 may be adjusted by rotating threaded screw 56 of inner collar 50 within apertured housing 40 so that inner collar 50 extends inwardly to a greater or lesser degree relative to housing 40. For example, if a greater degree of compression is required in order to ensure annular gland 54 sealingly engages tube inner end 17, inner collar 50 may be rotated within apertured housing 40 to reduce the displacement between annular sealing gland 54 and housing 40.

Probe 18 also includes an inward travel limit ring 72 which encircles wand 20 and is slidably adjustable along the longitudinal axis of wand 20 between knob 25 and the outer end of housing 40. Ring 72 is lockable at a selected axial position on wand 20 by turning thumb screw 74. Ring 72 limits axial travel of wand 20 and hence transducer 21 when wand 20 is slid inwardly.

Thumb screw 74 of ring 72 is aligned with transducer 21 so that it indicates the orientation of transducer 21 when wand 20 is rotated. For example, if probe 18 indicates that tube 10 is dangerously thin at a particular circumferential position, the exact clock position may be determined by noting the orientation of thumb screw 74.

Ring 72 may be positioned to enable inward travel of wand 20 for up to approximately 12 inches, but it is usually set to a restrict inward travel of wand 20 to two or three inches since this is ordinarily the region of tube 10 which is most prone to corrosion (i.e. the region of tube 10 directly proximate to lower drum outer surface 15).

An outer travel limit ring 84 may be provided for limiting outward travel of wand 20. Ring 84 encircles wand 20 and is slidable between transducer receptacle 30 and the innermost end of inner sealing collar 50. An allen screw 87 is provided for locking ring 84 at a selected axial position.

Optionally, a wire brush 82 may be mounted at the inner end of transducer receptacle 32 for brushing debris away from tube inner wall 17 when probe 18 is inserted and slidably reciprocated within tube 10.

In operation, probe 18 is initially prepared for use by connecting coaxial cable 35 extending from the outer end 24 of wand 20 to a standard, portable ultrasonic signal processing instrument. Probe 18 is then inserted into a calibration tube of known thickness filled with coupling liquid such as water. The ultrasonic instrument is then calibrated in a manner well known to those skilled in the art so that the time intervals between successive signals are accurately converted to thickness readings.

Figure 7:
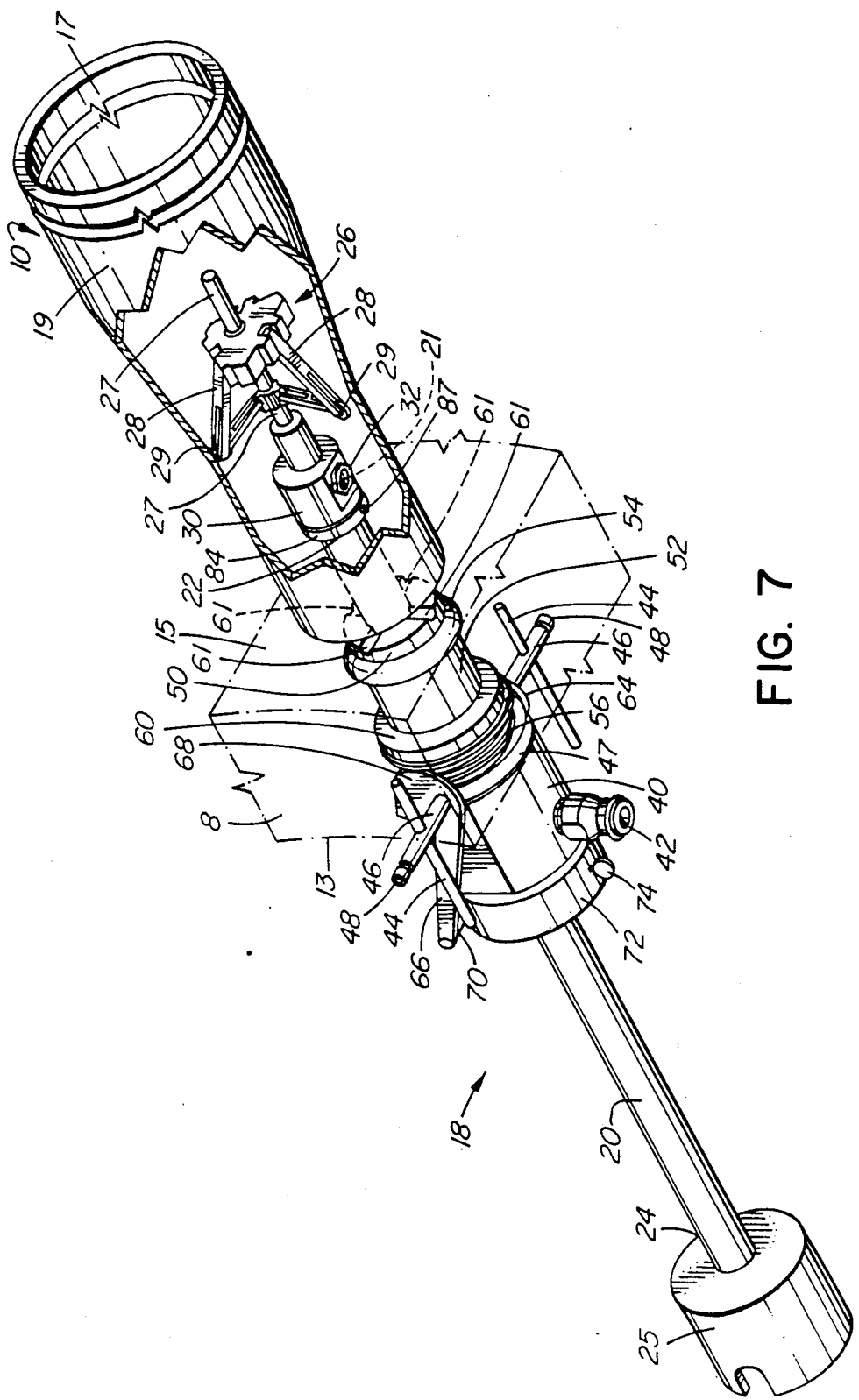
FIG. 7 is an isometric view of the probe of FIG. 4 inserted in operative position within a boiler tube shown in outline.
Figure 8:
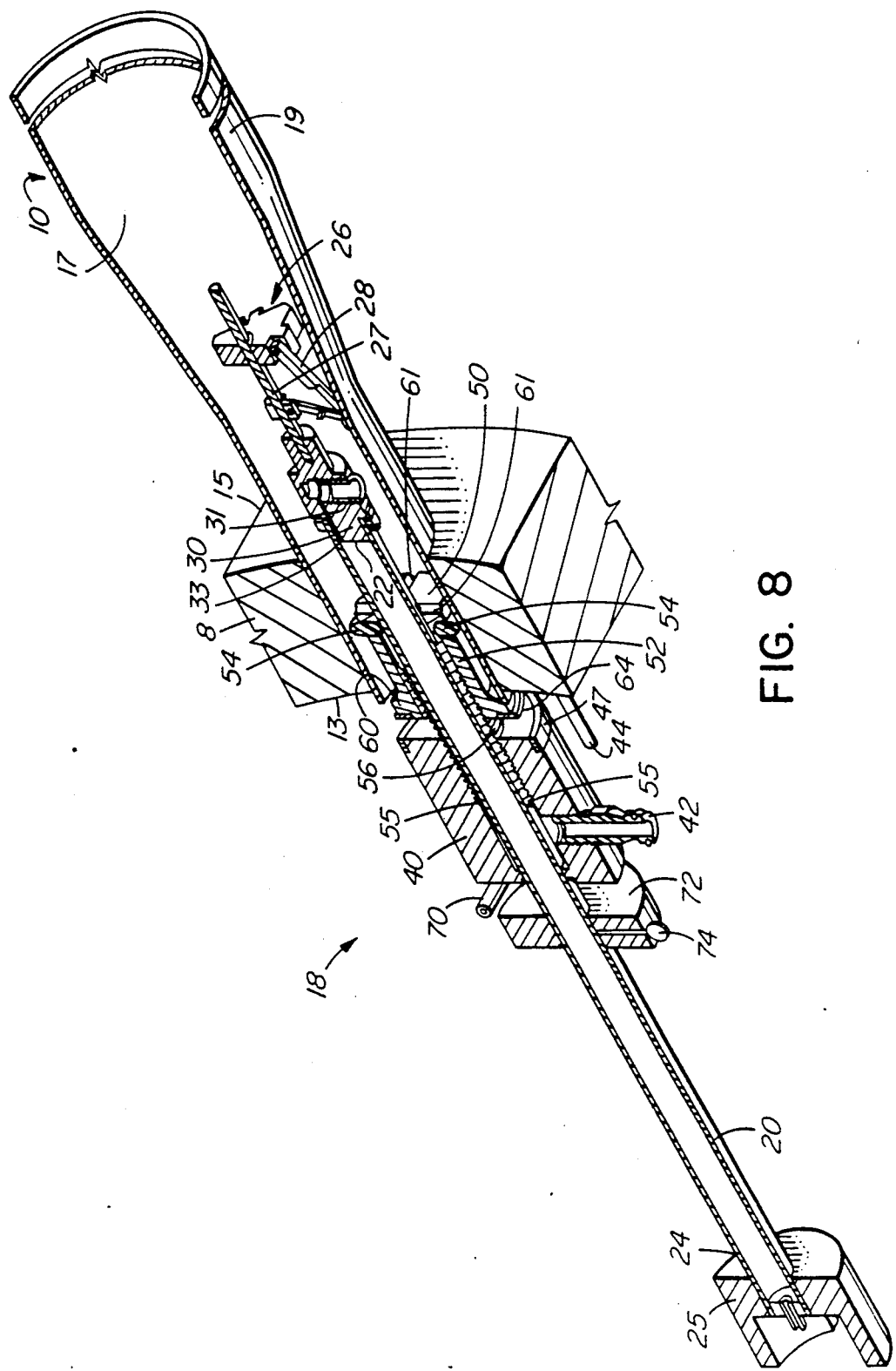
FIG. 8 is an isometric, longitudinal cut-away view of the probe of FIG. 7.

Probe 18 is then inserted into the open end 12 of the tube 10 to be inspected. This is manually performed by a maintenance inspector from within drum 8 as follows. Parallel rods 44 must first be adjusted to compensate for the wall thickness of the drum 8 in question. This is accomplished by loosening cap screws 48 and sliding rods 44 inwardly or outwardly as required. Cap screws 48 are then tightened to lock rods 44 at the selected position. Rods 44 are provided to ensure that ultrasonic scanning commences just outside the drum outer surface 15 and progresses inwardly, away from drum 8. To this end, the position of rods 44 is adjusted until the longitudinal displacement between the inner end of rods 44 and the center of transducer 21 approximates the thickness of drum 8 as previously determined by measurement. In the operative position, the inner ends of rods 44 contact the inner drum surface 13 to provide a constant offset (FIG. 7).

The next adjustment which must be made is to set inward travel limit ring 72 at a suitable axial position on wand 20 to limit the degree of inward travel of wand 20 and hence transducer 21. As discussed aforesaid, usually the degree of inward travel is limited to two or three inches commencing at drum outer surface 15 since this is ordinarily the region of greatest concern. Thumb screw lock 74 of ring 72 is orientated so that it is aligned with the center of transducer 21. This ensures that screw lock 74 accurately indicates the clock position of transducer 21 when wand 20 is rotated (transducer 21 is hidden from view in the operative scanning position illustrated in FIG. 7).

Sealing collars 50, 52 and annular sealing gland 54 must then be adjusted to seal the outer end 12 of tube 10. This is accomplished by rotating inner collar 50 relative to housing 40 to adjust the degree of compression of sealing gland 54 as described above. Locking arms 66 are then pivoted downwardly by manipulating handle 70 to lock the sealing assembly in place. In particular, the camming surface 68 of arms 66 is forced against cam bearing ring 64 to axially compress outer collar 52 as described above. Axial compression of outer collar 52 causes corresponding radial compression of annular gland 54 so that it sealingly engages tube inner surface 17 with a significant degree of force.

Once the aforesaid adjustments have been completed, coupling liquid may be then introduced into the tube 10 under inspection. A three-way valve accessory (not shown) is provided for regulating the flow of liquid to and from probe 18. The valve is connectable to a liquid supply hose extending from the liquid supply, a liquid delivery hose extending from the valve to the housing liquid inlet 42, and a liquid drain hose extending from the valve to a drain.

Before introducing water into tube 10, wand 20 is slid inwardly to its fully extended position and rotated until screw lock 74 indicates that transducer 21 is facing upwardly in the 12 o'clock position. The water supply is then turned on and the valve accessory is adjusted to enable flow of water through the supply and delivery hoses into housing liquid inlet 42. As shown best in FIG. 10, coupling liquid passes through liquid inlet 42 into the housing aperture and passes inwardly between wand 20 and inner sealing collar 50. Rod wiper seal 43 prevents the coupling liquid from leaking through the outer end of housing 40. Similarly, O-ring 55 prevents the coupling liquid from escaping through the housing inner end between housing 40 and the outer threaded surface 56 of inner collar 50.

The coupling liquid passes through the inner end of inner collar 50 through slots 61 (FIG. 7) to flood tube 10. Since tube 10 is ordinarily upwardly inclined, the coupling liquid collects at the tube outer end 12 proximate drum 8 and is maintained there by gravitational forces. Tube 10 usually fills with a suitable volume of water within 5-10 seconds, depending upon the water pressure and the tube inclination. An adequate volume of water is indicated by a series of steady signals appearing on the cathode ray tube display of the ultrasonic instrument. It is important not to overfill tube 10 since this may cause excessive water pressure build-up which could unseat annular gland 54 from its radially compressed position against the tube inner surface 17.

Once tube 10 is suitably filled with coupling liquid, the wand knob 25 may be manipulated to cause scanning movement of transducer 21. The recommended scanning technique is to withdraw wand 20 outwardly to its fully retracted position while simultaneously holding locking arm handle 70 to ensure that probe 18 does not inadvertently slip out of tube 10.

Depending on the thickness of drum 8, outward travel limit ring 84 may be positioned to limit outward travel of wand 20. Otherwise, wand 20 is fully withdrawn until the outer end of transducer receptacle 30 contacts the inner end of inner sealing collar 50. Wand 20 is initially positioned with thumb screw lock 74 of inward travel ring 72 extending upwardly so that transducer 21 is at the 12 o'clock position. The inspector then proceeds to rotate wand 20 slowly for 360° until the transducer 21 returns to the 12 o'clock position. Wand 20 is then advanced approximately ¼ of an inch and the rotary scan is repeated. Ordinarily the direction of rotation is alternated to minimize twisting of coaxial cable 35. The above procedure is repeated until the preselected maximum inward travel limit of wand 20 is reached (i.e. until inward travel limit ring 72 bears against the outer surface of housing 40).

Ordinarily the operator will then proceed to specific areas where low readings were noted. An important feature of the applicant's invention is that wand 20 may be skewed relative to the longitudinal centerline of tube 10 by pivoting wand 20 relative to annular gland 54. This is possible since there is some clearance between the outer surface of outer collar 52 and tube inner surface 17. Outer collar flange 60 is also spaced apart a short distance from the outermost end 12 of tube 10 in order to provide clearance for pivotal movement (FIG. 10).

It is also important that self-centering device 26 mounted at the inner end of probe 18 is resiliently biased. Thus probe 18 is free for pivotable movement at both its inner and outer ends. The operator need only manipulate wand knob 25 to cause wand 20 to skew away from its ordinary scanning position coaxial with tube 10. When forced manual pressure on knob 25 is released, self-centering device 26 will bias wand 20 back to the ordinary scanning position coaxial with tube 10.

By skewing wand 20 away from a scanning position coaxial with tube 10 it is possible to measure the thickness of irregular regions of tube inner wall 17 which are not parallel to the centerline of tube 10. In other words, wand 20 may be manipulated so that the ultrasonic pulses transmitted by transducer 21 are directed at tube inner wall 17 at a plurality of oblique angles. Accordingly, corroded tube areas which are not parallel to the centerline of the tube may be readily detected using the applicant's invention. This results in more accurate and reliable data.

As should be apparent to someone skilled in the art, the tube thickness readings may be manually noted or automatically logged to a computer processor.

After a particular tube 10 has been inspected, wand 20 is pulled outwardly to its fully retracted position and tube 10 is drained of coupling liquid. This is accomplished by adjusting the above-noted valve accessory to enable delivery of liquid from probe 18 to a remote drain (preferably through a transparent hose so that drainage may be visually monitored).

After tube 10 has been completely drained, the seal gland assembly is unlocked by pivoting cam handle 70 relative to housing 40. This releases the compressive forces urging annular gland 54 against the tube inner wall 17 so that probe 18 may be manually withdrawn from tube 10 by the operator. Probe 18 is then inserted into another tube 10 and the above-described procedure is repeated. The entire scanning procedure usually takes on the order of 5 minutes per tube 10.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A hand-held probe for inspecting the thickness of an elongate conduit having an open outer end in communication with the interior of a drum, comprising:
   (a) an apertured housing;
   (b) an elongate hollow wand having an inner end and an outer end, wherein said wand is adapted for sliding reciprocal movement through said housing along the longitudinal axis of said conduit and for rotational movement relative to said housing and said conduit,
   (c) a transducer for transmitting and receiving ultrasonic signals mounted at said wand inner end transversely of the wand longitudinal axis, wherein said transducer is connectable to an ultrasonic signal processing instrument remote from said probe;
   (d) sealing means encircling said wand at an axial position thereof for releasably sealing said conduit outer end;
   (e) liquid delivery means connectable to an inlet on said housing for providing coupling liquid to and drawing said liquid from a portion of said conduit above said sealing means which includes said transducer;
   (f) self-centering means coupled to the inner end of said wand for centering said wand coaxially with said conduit, such that ultrasonic pulses generated by said transducer are ordinarily transmitted in a path normal to the inner surface of said conduit;
wherein said wand is manually pivotable about said sealing means away from a scanning position coaxial with said conduit to a scanning position offset from the longitudinal axis of said conduit, such that said ultrasonic pulses generated by said transducer are transmitted in a path oblique to said conduit inner surface.

2. A probe as defined in claim 1, wherein said sealing means encircles said wand at an axial position between said transducer and said housing.

3. A probe as defined in claim 2, wherein said sealing means comprises:
   (a) an inner collar threadedly connectable to the inner end of said housing, said inner collar having a radial groove at a position remote from said housing;
   (b) a resiliently deformable annular gland positionable in said inner collar groove for radially engaging said conduit inner surface; and
   (c) an outer collar surrounding a central portion of said inner collar, said outer collar having an inner end bearing against said annular gland.

4. A probe as defined in claim 3, wherein the outer diameter of said outer collar is less than the inner diameter of said conduit.

5. A probe as defined in claim 3, wherein said outer collar has an outer end having an outer diameter greater than said conduit inner diameter.

6. A probe as defined in claim 3, further comprising compression means connected to said housing for axially compressing said outer collar to cause radial compression of said annular gland against said conduit inner surface.

7. A probe as defined in claim 6, wherein said compression means comprises a pair of arms pivotally coupled to said housing on opposite lateral sides thereof, each of said arms having an inner camming surface bearing against outer collar.

8. A probe as defined in claim 7, wherein said compression means further comprises a handle extending between said arms for actuating simultaneous pivotal movement of said arms.

9. A probe as defined in claim 6, wherein said inner collar is rotatable relative to said housing to adjust the longitudinal displacement between said compression means and said annular gland.

10. A probe as defined in claim 1, wherein the outer end of said housing sealingly engages said wand.

11. A probe as defined in claim 1, wherein said self-centering means comprises a tripod encircling said wand, said tripod having spaced-apart radially extensible and retractable arms for frictionally engaging said conduit inner surface.

12. A probe as defined in claim wherein said tripod arms are biased to said extended position.

13. A probe as defined in claim 1, further comprising an enlarged handle located at said wand outer end to enable manual manipulation of said wand.

14. A probe as defined in claim 13, further comprising an inward travel limit ring encircling said wand and slidably adjustable along the longitudinal axis thereof between said housing and said handle and lockable at a selected axial position thereof.

15. A probe as defined in claim 14, wherein said limit ring has a marking at one circumferential position thereof alignable with said transducer for indicating the orientation of said transducer when said wand is rotated within said conduit.

16. A probe as defined in claim 1, further comprising an outward travel limit ring encircling said wand and slidable along the longitudinal axis thereof between said transducer and said sealing means, wherein said ring is lockable at a selected axial position on said wand.

17. A probe as defined in claim 1, further comprising a pair of elongate rods mounted on opposed sides of said housing in a plane generally parallel to the longitudinal axis of said housing, wherein said rods are longitudinally adjustable relative to said housing such that the inner ends of said rods contact the inner surface of said drum on either side of said conduit when said probe is placed in operative scanning position within said tube.

* * * * *